(12) United States Patent
Wang

(10) Patent No.: US 11,918,373 B2
(45) Date of Patent: Mar. 5, 2024

(54) SYSTEMS AND METHODS FOR SCREENING, DIAGNOSIS AND MONITORING SLEEP-DISORDERED BREATHING

(71) Applicant: ResMed Pty Ltd, Bella Vista (AU)

(72) Inventor: Ning Wang, Glenwood (AU)

(73) Assignee: ResMed Pty Ltd (AU)

( * ) Notice: Subject to any disclaimer, the term of this patent is extended or adjusted under 35 U.S.C. 154(b) by 0 days.

(21) Appl. No.: 18/080,983

(22) Filed: Dec. 14, 2022

(65) Prior Publication Data
US 2023/0210452 A1    Jul. 6, 2023

Related U.S. Application Data

(63) Continuation of application No. 15/572,964, filed as application No. PCT/AU2016/050346 on May 9, 2016, now Pat. No. 11,771,365.
(Continued)

(51) Int. Cl.
*A61B 5/00* (2006.01)
*A61B 5/0205* (2006.01)
(Continued)

(52) U.S. Cl.
CPC .......... *A61B 5/4809* (2013.01); *A61B 5/0205* (2013.01); *A61B 5/036* (2013.01);
(Continued)

(58) Field of Classification Search
None
See application file for complete search history.

(56) References Cited

U.S. PATENT DOCUMENTS

| 4,944,310 A | 7/1990 | Sullivan |
| 6,532,959 B1 | 3/2003 | Berthon-Jones |

(Continued)

FOREIGN PATENT DOCUMENTS

| JP | 2005124858 A | 5/2005 |
| JP | 2012503804 A | 2/2012 |

(Continued)

OTHER PUBLICATIONS

Office Action issued in corresponding Japanese Patent Application No. 2021-163949, dated Apr. 14, 2023, 10 pages.
(Continued)

*Primary Examiner* — Kaylee R Wilson
*Assistant Examiner* — Jairo H Portillo
(74) *Attorney, Agent, or Firm* — Botos Churchill IP Law LLP

(57) ABSTRACT

A method and system are disclosed for use in monitoring/screening/diagnosing sleep or wake state of a subject or patient. The method generally includes monitoring the patient's activity during one or more sleep sessions comprising a plurality of intervals known as epochs. The sleep/wake state of the subject is determined during each epoch of the session using actigraphy data obtained during the monitoring session. The actigraphy data provides information about the activity of a patient during an epoch. The sleep or wake state is determined based on a ratio of the activity count during an epoch to the activity count during a preceding epoch. If the ratio is greater than a first activity threshold, then a "wake" indication may be provided by, for example, the system. Alternatively, or additionally, a "wake" indication may be determined if the activity count during the epoch is greater than a threshold.

24 Claims, 10 Drawing Sheets

Related U.S. Application Data

(60) Provisional application No. 62/160,937, filed on May 13, 2015.

(51) Int. Cl.
    *A61B 5/03*     (2006.01)
    *A61B 5/087*    (2006.01)
    *A61B 5/097*    (2006.01)
    *A61B 5/11*     (2006.01)
    *A61B 5/113*    (2006.01)
    *A61B 5/30*     (2021.01)
    *A61B 5/389*    (2021.01)

(52) U.S. Cl.
    CPC .............. *A61B 5/087* (2013.01); *A61B 5/097* (2013.01); *A61B 5/1118* (2013.01); *A61B 5/113* (2013.01); *A61B 5/30* (2021.01); *A61B 5/389* (2021.01); *A61B 5/4815* (2013.01); *A61B 5/4818* (2013.01); *A61B 5/6819* (2013.01); *A61B 5/7278* (2013.01); *A61B 5/7282* (2013.01); *A61B 5/4519* (2013.01); *A61B 2562/0247* (2013.01)

(56) References Cited

U.S. PATENT DOCUMENTS

| | | |
|---|---|---|
| 7,361,146 B1 | 4/2008 | Bharmi |
| 8,821,418 B2 | 9/2014 | Meger et al. |
| 2002/0183644 A1 | 12/2002 | Levendowski et al. |
| 2005/0209644 A1 | 9/2005 | Miesel et al. |
| 2006/0150975 A1 | 7/2006 | Sullivan |
| 2006/0266356 A1 | 11/2006 | Sotos et al. |
| 2006/0270949 A1 | 11/2006 | Mathie et al. |
| 2007/0129769 A1 | 6/2007 | Bourget et al. |
| 2008/0300449 A1 | 12/2008 | Gerber et al. |
| 2009/0203972 A1 | 8/2009 | Heneghan et al. |
| 2010/0100004 A1 | 4/2010 | Van Someren |
| 2010/0152543 A1 | 6/2010 | Heneghan |
| 2010/0240982 A1 | 9/2010 | Westbrook et al. |
| 2012/0232414 A1 | 9/2012 | Mollicone et al. |
| 2013/0310662 A1 | 11/2013 | Tsutsumi et al. |
| 2014/0088373 A1 | 3/2014 | Phillips et al. |
| 2014/0116440 A1 | 5/2014 | Thompson |
| 2014/0309709 A1 | 10/2014 | Gozani et al. |
| 2014/0364770 A1 | 12/2014 | Slonneger et al. |
| 2014/0371547 A1 | 12/2014 | Gartenberg et al. |
| 2015/0250963 A1 | 9/2015 | Ramanan |

FOREIGN PATENT DOCUMENTS

| | | |
|---|---|---|
| JP | 2012532703 A | 12/2012 |
| JP | 2014008159 A | 1/2014 |
| WO | 2010036700 A1 | 4/2010 |
| WO | 2010107928 A2 | 9/2010 |
| WO | 2011006199 A1 | 1/2011 |
| WO | 2013177621 A1 | 12/2013 |
| WO | 2014029764 A1 | 2/2014 |
| WO | 2015120522 A1 | 8/2015 |
| WO | 2015131065 A1 | 9/2015 |

OTHER PUBLICATIONS

"Count (Verb) American English Definition and Synonyms: Macmillan Dictionary." Count (Verb) American English Definition and Synonyms, 2021.

Chen, Lyn Chao-ling, et al. "A Sleep Monitoring System Based On Audio, Video and Depth Information for Detecting Sleep Events", 2014 IEEE International conference on Multimedia and Expo (ICME), IEEE, pp. 1-6, Jul. 14, 2014.

Galland, Barbara C., et al. "Algorithms for using an activity-based accelerometer for identification of infant sleep-wake states during nap studies", Sleep Medicine 13, pp. 743-751 (2012).

Hwang, Su Hwan, et al. "Sleep period time estimation based on electrodermal activity." IEEE journal of biomedical and health informatics 21.1 (2015): 115-122. (Year: 2015).

JP Office Action dated Jan. 14, 2021 for JP Patent Application No. 2017-559054.

JP Office Action dated May 29, 2020 for JP Patent Application No. 2017-559054.

Non-Final Office Action dated Jun. 27, 2019.

Office Action issued in Japanese Patent Application No. 2021-163949 dated Sep. 6, 2022, 24 pages.

Supplementary European Search report dated Nov. 8, 2018 for PCT/AU2016/050346.

Chen, Chao-Ling , et al., "A Sleep Monitoring Systems Based On Audio, Video And Depth Information For Detecting Sleep Events," EEE International Conference on Multimedia and Expo, Sep. 8, 2014.

West, John B., "Respiratory Physiology", Lippincott Williams & Wilkins, 9th Edition published 2012.

International Search Report for Application No. PCT/AU2016/050346 dated Jul. 20, 2016.

SYSTEMS AND METHODS FOR SCREENING, DIAGNOSIS AND MONITORING SLEEP-DISORDERED BREATHING

1 CROSS-REFERENCE TO RELATED APPLICATIONS

This application is a continuation of U.S. patent application Ser. No. 15/572,964 filed Nov. 9, 2017, which is a national phase entry under 35 U.S.C. § 371 of International Application No. PCT/AU2016/050346 filed May 9, 2015, published in English, which claims priority from U.S. Provisional Patent Application No. 62/160,937, filed May 13, 2015, all of which are incorporated herein by reference

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE TECHNOLOGY

5.1 Field of the Technology

The present technology relates to one or more of the screening, diagnosis, and monitoring of respiratory-related disorders. The present technology also relates to medical devices or systems, and their use.

5.2 Description of the Related Art 5.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The primary function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g., apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods known as apneas, typically of 30 to 120 seconds in duration, sometimes 200 to 300 times per night. OSA often causes excessive daytime somnolence, and it may cause cardiovascular disease and brain damage. OSA is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

5.2.2 Diagnosis and Monitoring Systems

Clinical experts may be able to screen, diagnose, or monitor patients adequately based on personal observation. However, there are circumstances where a clinical expert may not be available, or a clinical expert may not be affordable. In some circumstances different clinical experts may disagree on a patient's condition. A given clinical expert may apply a different standard at different times. With a busy clinical practice, a clinician may have difficulty keeping up with evolving patient management guidelines.

Polysomnography (PSG) is a conventional system for diagnosis and prognosis of cardio-pulmonary disorders, and typically involves expert clinical staff to both apply and interpret. PSG typically involves the placement of 15 to 20 contact sensors on a person in order to record various bodily signals such as electroencephalography (EEG), electrocardiography (ECG), electrooculograpy (EOG), electromyography (EMG), etc. However, while they may be suitable for their usual application in a clinical setting, such systems are complicated and potentially expensive, and/or may be uncomfortable or impractical for a patient at home trying to sleep.

A more convenient screening/diagnosis/monitoring system for home use comprises a nasal cannula, a pressure sensor, a processing device, and recording means. A nasal cannula is a device comprising two hollow open-ended projections that are configured to be inserted non-invasively a little way into a patient's nares so as to interfere as little as possible with the patient's respiration. The hollow projections are in fluid communication with a pressure transducer via a Y-shaped tube. The pressure transducer provides a data signal representative of the pressure at the entrance to the patient's nares (the nasal pressure). Nasal pressure is a satisfactory proxy for the nasal flow rate because the nasal pressure signal is comparable in shape to a nasal flow rate signal.

The processing device may be configured to analyse the nasal pressure signal from the pressure transducer in real time in order to monitor the patient's breathing. By contrast, diagnosis need not be performed in real time. The recording means is therefore configured to record the nasal pressure signal from the pressure transducer for later off-line analysis for diagnosis purposes.

The analysis of the nasal pressure signal may seek to identify apneas and hypopneas during a screening/diagnosis/monitoring session. The total number of apneas and hypopneas divided by the length of the monitoring session gives an index of severity of SDB known as the apnea-hypopnea index (AHI). AHI is a widely-used screening and diagnostic tool for sleep-disordered breathing. However, such analysis tends to underestimate the AHI, since for significant periods during the session the patient may not have been asleep. The result is that screening patients based on the AHI returned by such analysis tends to miss the patients whose sleep during the monitoring session was patchy, as often occurs for example with insomniacs.

A more accurate method of estimating the AHI divides the number of apneas and hypopneas by the number of hours the patient was asleep during the session. To compute the AHI in this way requires the analysis to detect when the patient was asleep. Detecting sleep/wake state purely from nasal pressure (or indeed from the signal for which it is a proxy, nasal flow rate) has proven to be a difficult task, with consequent effects on the accuracy of AHI calculation and hence AHI-based screening, diagnosis, and monitoring.

A need therefore exists for an improved SDB screening/monitoring/diagnosis system that more accurately estimates the total sleep time of the patient.

6 BRIEF SUMMARY OF THE TECHNOLOGY

The present technology is directed towards providing medical devices used in the monitoring or diagnosis of respiratory disorders having one or more of improved comfort, cost, efficacy, ease of use and manufacturability.

A first aspect of the present technology relates to systems for the screening, diagnosis, or monitoring of a respiratory disorder.

Another aspect of the present technology relates to methods used in the screening, diagnosis, or monitoring of a respiratory disorder.

One form of the present technology comprises methods and systems configured to estimate an amount of time the patient was asleep during a monitoring session using actigraphy data gathered during the session. The estimate may be used to compute an index of severity of sleep-disordered breathing (e.g. an apnea-hypopnea index (AHI)) for the session. Optionally, the estimate may take into account respiratory flow rate or effort data gathered during the session.

According to one aspect of the present invention, there is disclosed a method of estimating a total sleep time of a patient during a monitoring session comprising a plurality of epochs. The method comprises: determining a sleep/wake state of the patient during each epoch of the session using an actigraphy signal of the patient obtained during the monitoring session, and estimating the total sleep time from the sleep/wake state of the patient during each epoch. The determination of the sleep/wake state of the patient during an epoch comprises: determining an activity count for each epoch from the actigraphy signal, and determining the sleep/wake state of the patient during the epoch to be "wake" if a ratio of the activity count for the epoch to the activity count for a preceding epoch is greater than a first activity threshold.

According to another aspect of the present invention, there is disclosed a system for estimating a total sleep time of a patient during a monitoring session comprising a plurality of epochs. The system comprises: an actigraph configured to generate an actigraphy signal representing acceleration of the actigraph in each of three orthogonal axes; and a processor programmed to: determine an activity count for each epoch from the actigraphy signal; determine a sleep/wake state of the patient during each epoch to be "wake" if a ratio of the activity count for the epoch to the activity count for a preceding epoch is greater than a first activity threshold; and estimate the total sleep time from the sleep/wake state of the patient during each epoch.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE DRAWINGS

The present technology is illustrated by way of example, and not by way of limitation, in the figures of the accompanying drawings, in which like reference numerals refer to similar elements including:

Figure 3:
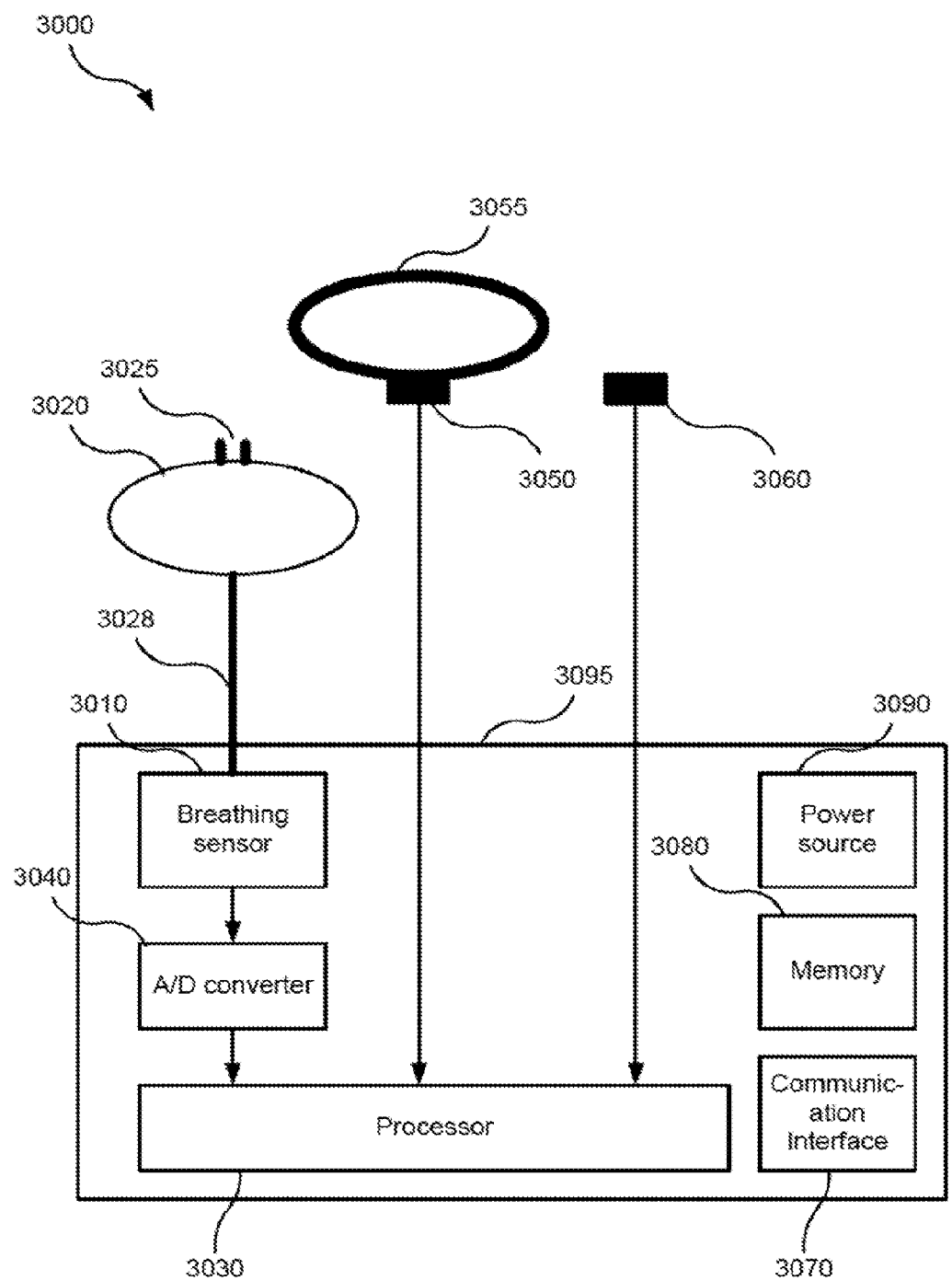
FIG. 3 is a block diagram of a screening/diagnosis/monitoring system in one form of the present technology.
Figure 5:
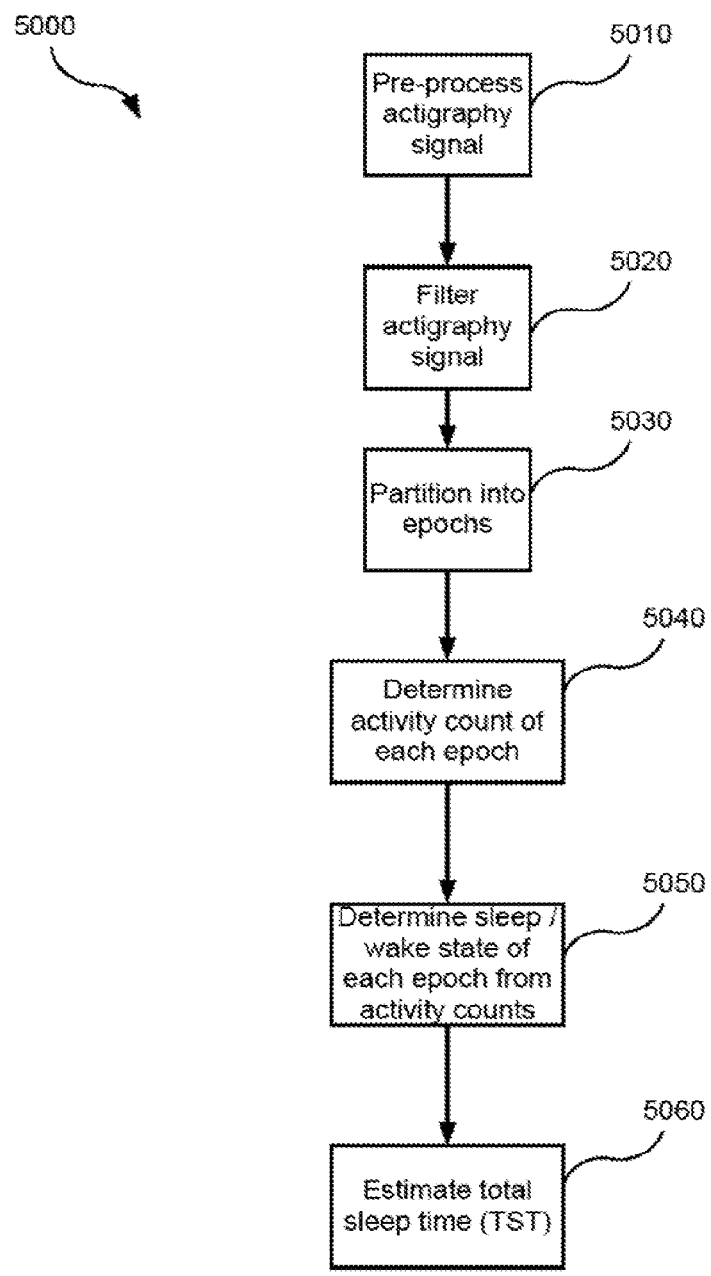

FIG. 5 contains a flow chart illustrating a method that may be used to implement the total sleep time estimation algorithm carried out by the system of FIG. 3 in one form of the present technology.

Figure 6:
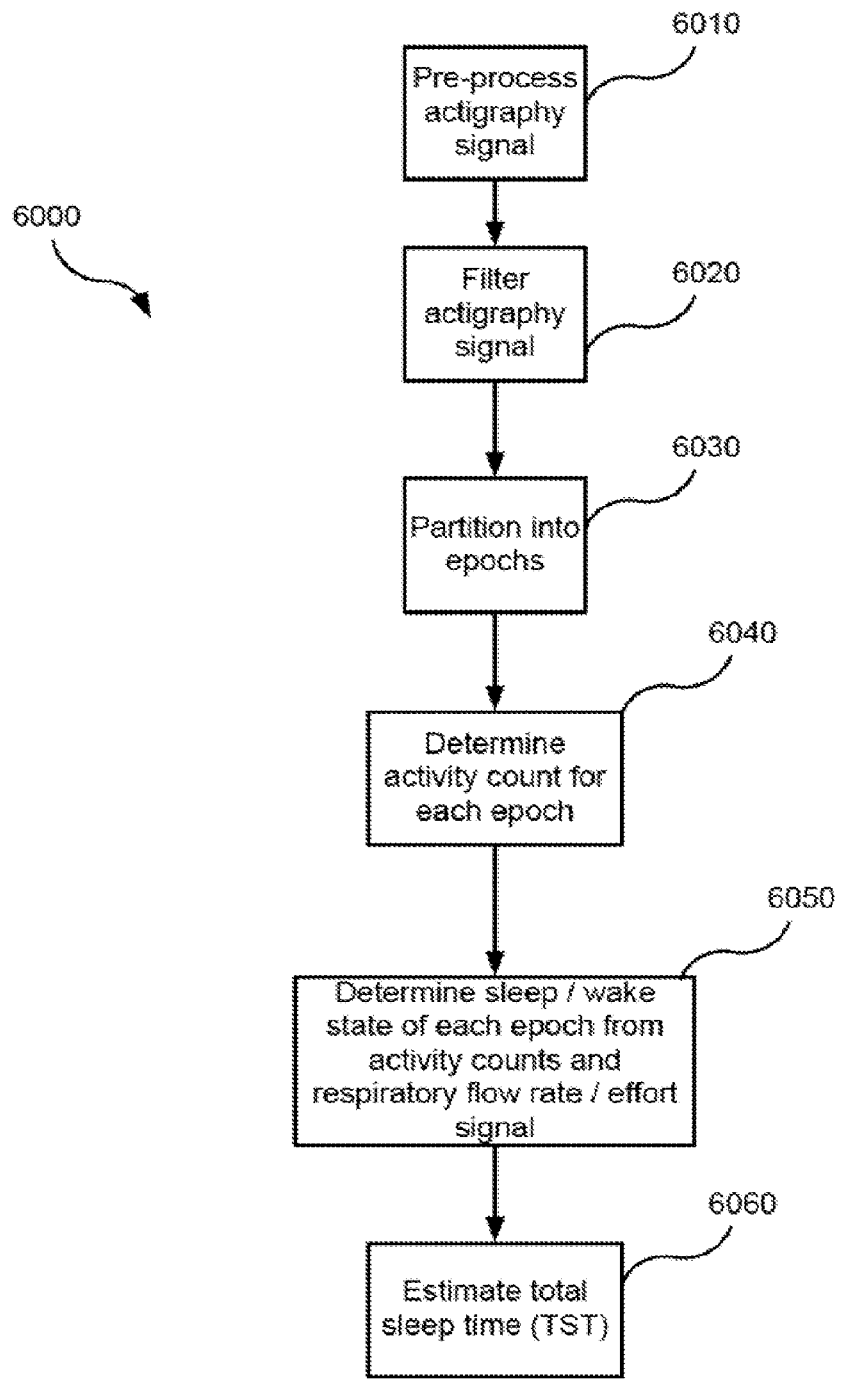

FIG. 6 contains a flow chart illustrating a method that may be used to implement the total sleep time estimation algorithm carried out by the system of FIG. 3 in an alternative form of the present technology.

Figure 7:
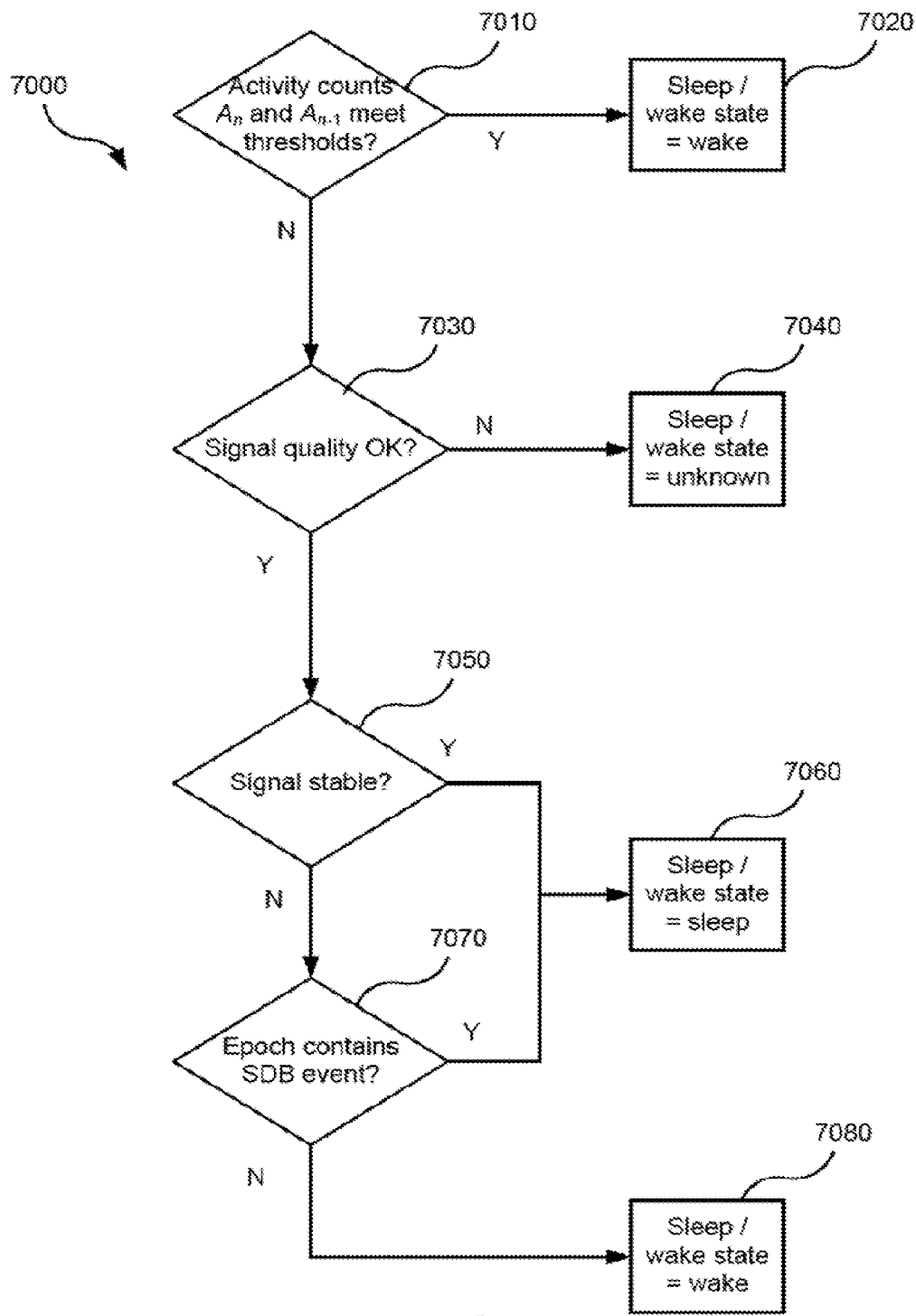

FIG. 7 contains a flow chart illustrating a method that may be used to implement the sleep/wake determination step of the method of FIG. 6.

Figure 8:
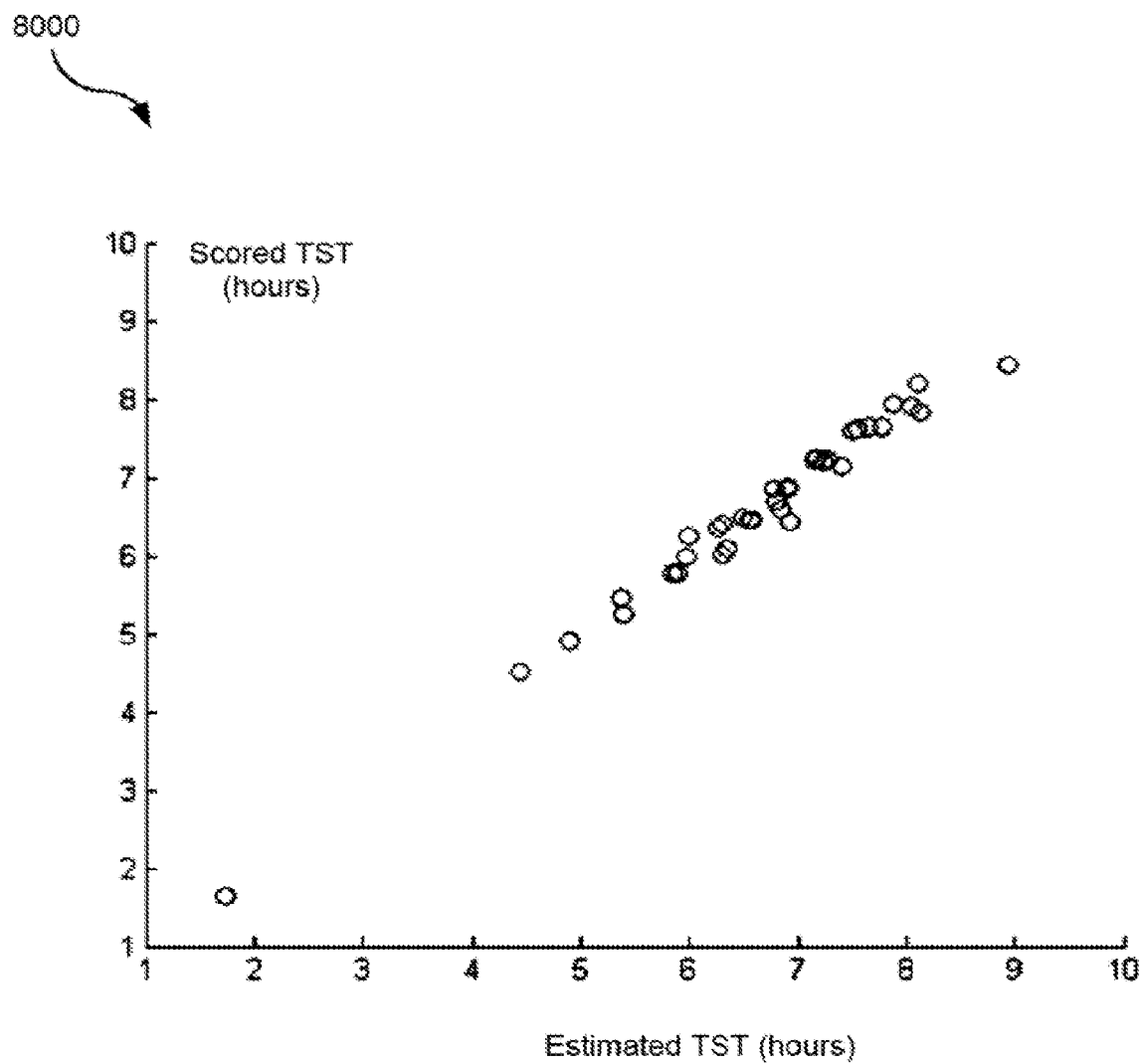

FIG. 8 contains a graph of total sleep time (TST) estimated using the algorithm of FIG. 5 plotted against scored TST values approximately 36 monitoring sessions.

Figure 9A:
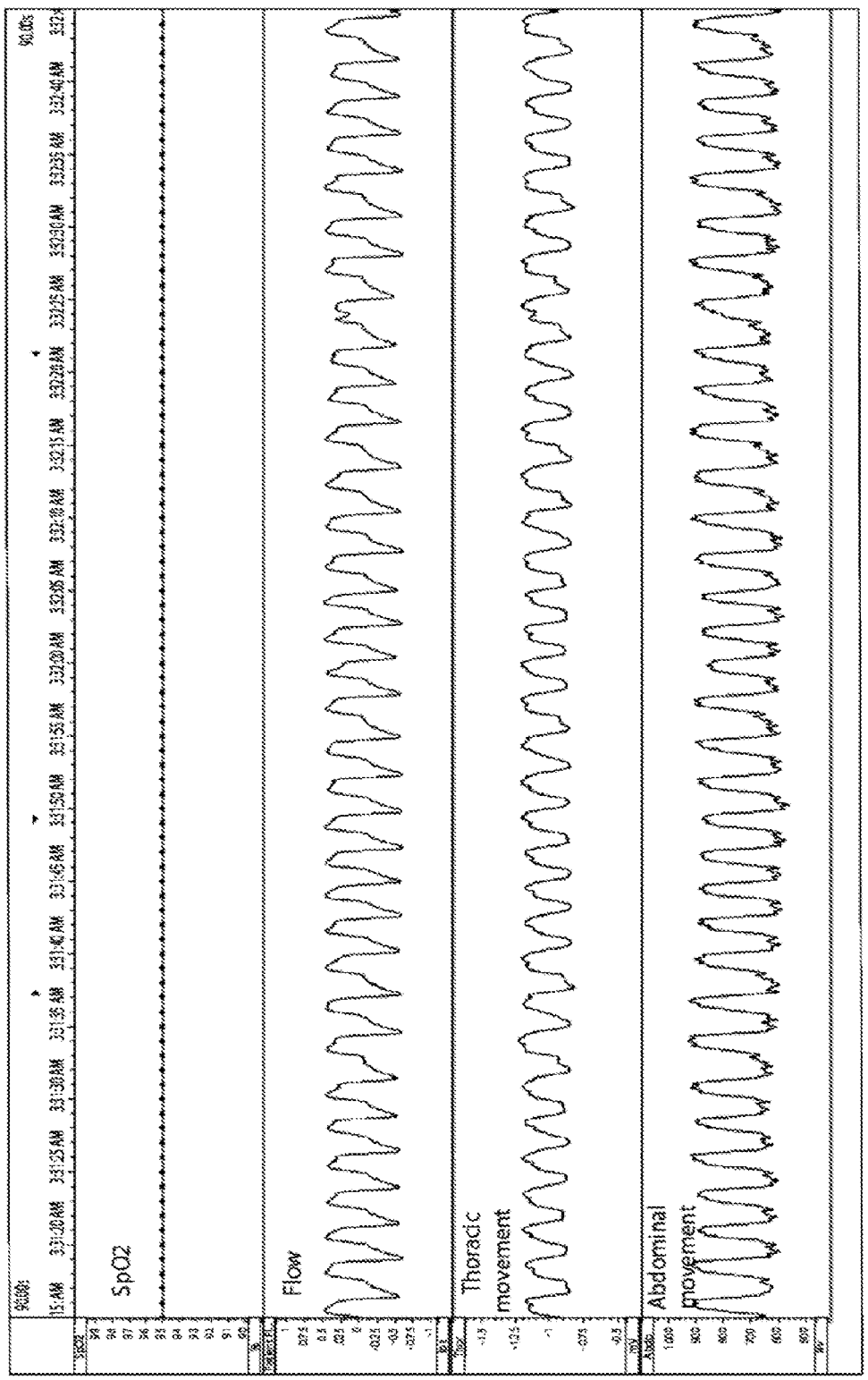

FIG. 9A shows polysomnography of a patient during non-REM sleep breathing normally over a period of about ninety seconds.

Figure 9B:
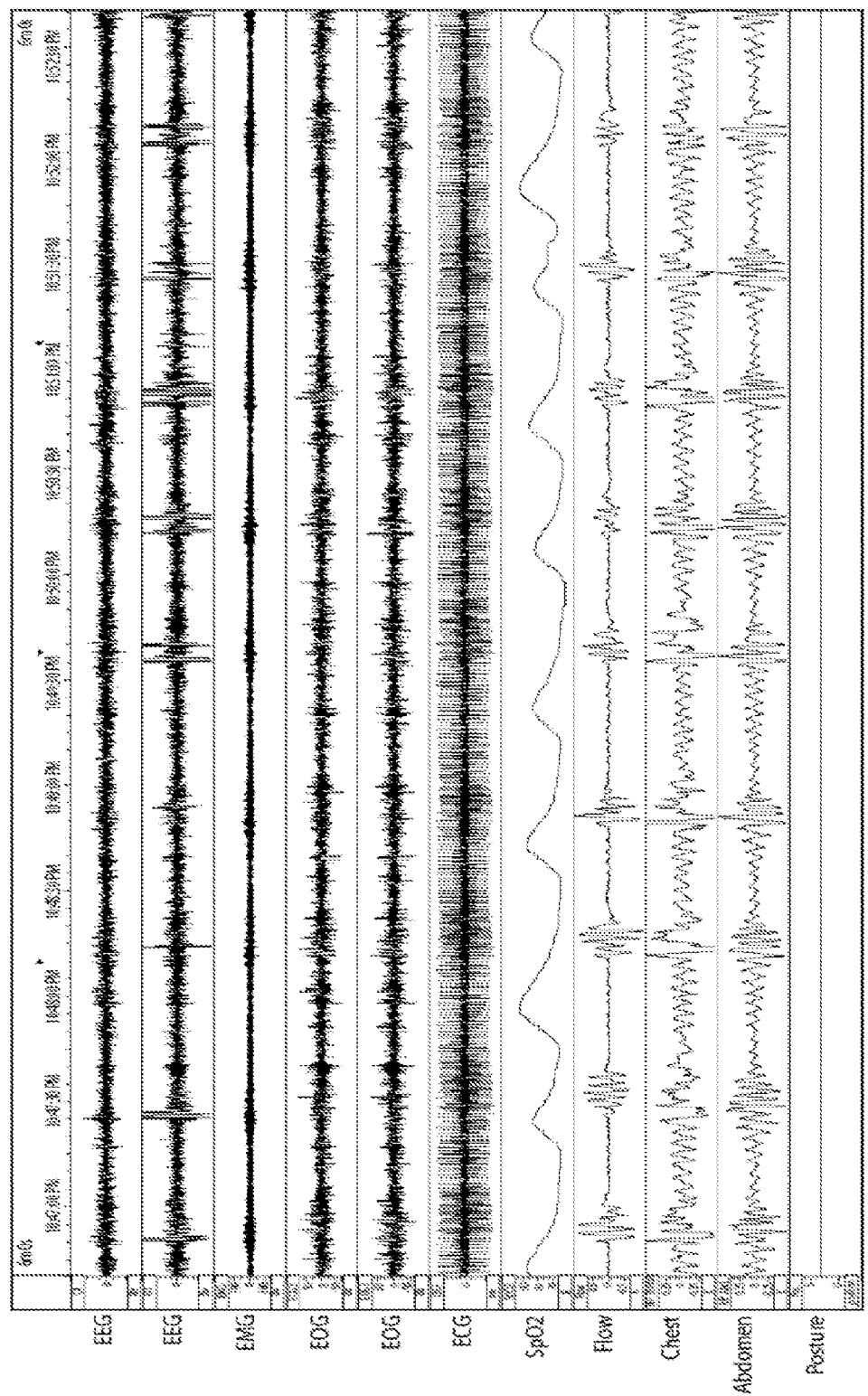

FIG. 9B shows polysomnography of a patient with sleep-disordered breathing over a period of about six minutes.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

8.1 SCREENING, DIAGNOSIS, MONITORING SYSTEMS

8.1.1 Polysomnography System

Figure 1:
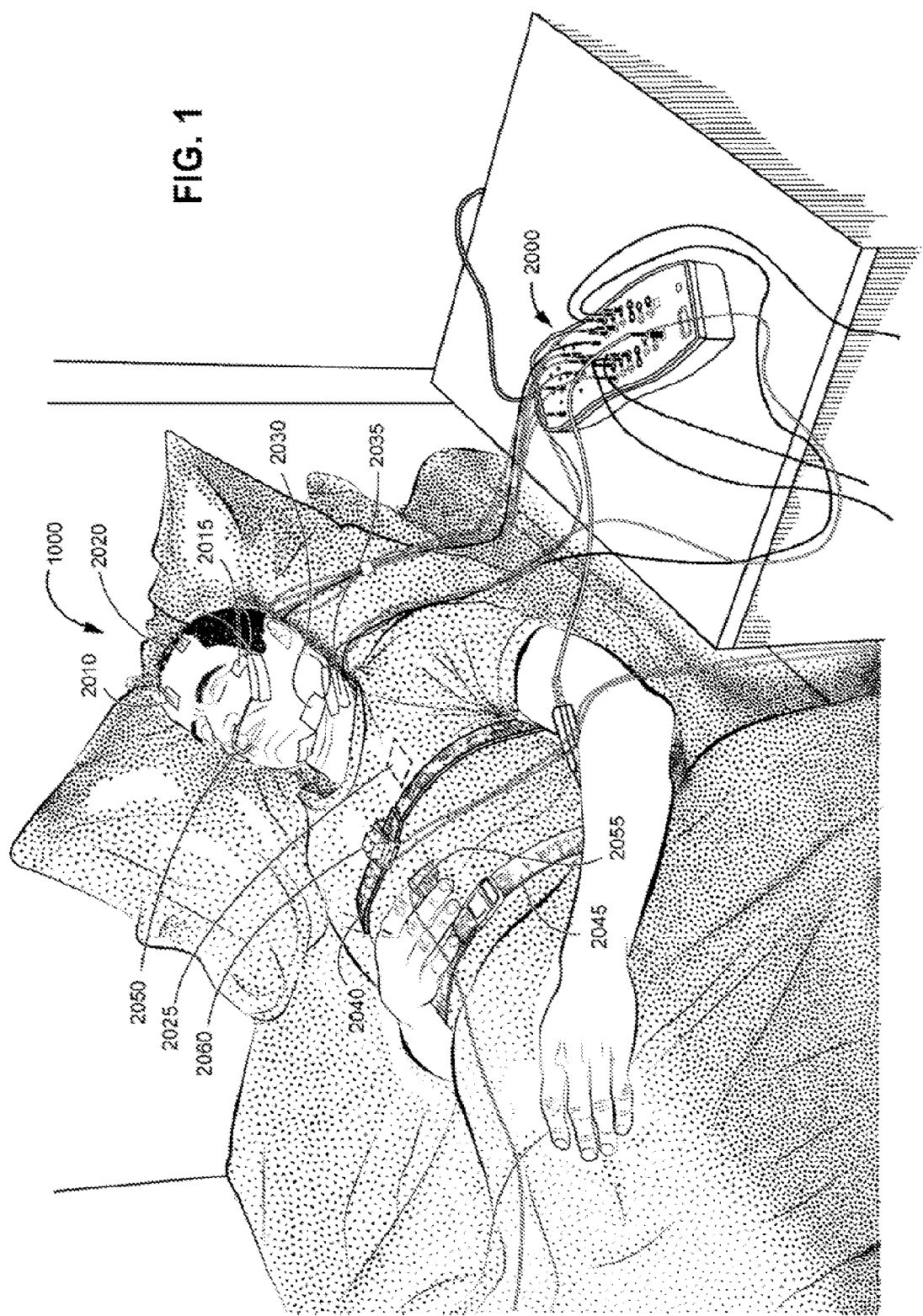
FIG. 1 shows a patient undergoing polysomnography (PSG).

FIG. 1 shows a patient 1000 undergoing polysomnography (PSG). A PSG system comprises a headbox 2000 which receives and records signals from the following sensors: an EOG electrode 2015; an EEG electrode 2020; an ECG electrode 2025; a submental EMG electrode 2030; a snore sensor 2035; a respiratory inductance plethysmogram (respiratory effort sensor) 2040 on a chest band; a respiratory inductance plethysmogram (respiratory effort sensor) 2045 on an abdominal band; an oro-nasal cannula and thermistor 2050; a photoplethysmograph (pulse oximeter) 2055; and a body position sensor 2060. The electrical signals are referred to a ground electrode (ISOG) 2010 positioned in the centre of the forehead.

8.1.2 System for Home Use

Figure 4:
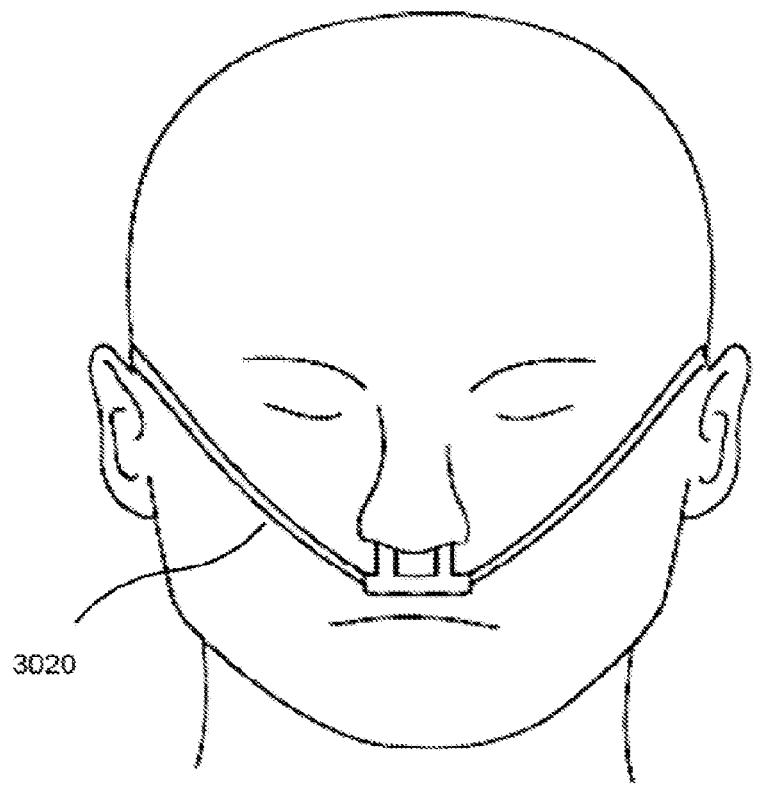
FIG. 4 illustrates a nasal cannula that may be used to implement the nasal cannula of the system of FIG. 3.

FIG. 3 is a block diagram illustrating a screening/diagnosis/monitoring system 3000 particularly suitable for home use. The system 3000 comprises a breathing sensor 3010 configured to generate an analog or digital signal indicative of the patient's breathing. In one implementation, the system 3000 comprises a nasal cannula 3020 configured to capture and convey a signal representing the patient's nasal pressure to the breathing sensor 3010 when connected to the system 3000. The nasal cannula 3020 comprises two prongs or nozzles 3025 configured to be inserted in the patient's nares as illustrated in FIG. 4. The prongs 3025 of the nasal cannula 3020 are connected to a flexible catheter 3028 that is configured to convey the pressure at the nares to the breathing sensor 3010, which is a pressure sensor in this implementation. The nasal pressure signal provided by the breathing sensor 3010 may be taken as representative of the patient's respiratory flow rate Qr, with appropriate conversion of units.

The system 3000 further comprises a processor 3030, configured to process and/or analyze the breathing signal derived from the patient's breathing and generated by the sensor 3020 as described below. The processor 3030 processes and/or analyzes the breathing signal in collaboration with the memory 3080.

The breathing sensor 3010 may be coupled to the processor 3030 via an A/D converter 3040, which converts the analog signal generated by the breathing sensor 3010 to a stream of digital data. Alternatively, if the breathing sensor 3010 is configured to generate a digital signal, the A/D converter 3040 may be omitted.

Figure 2:
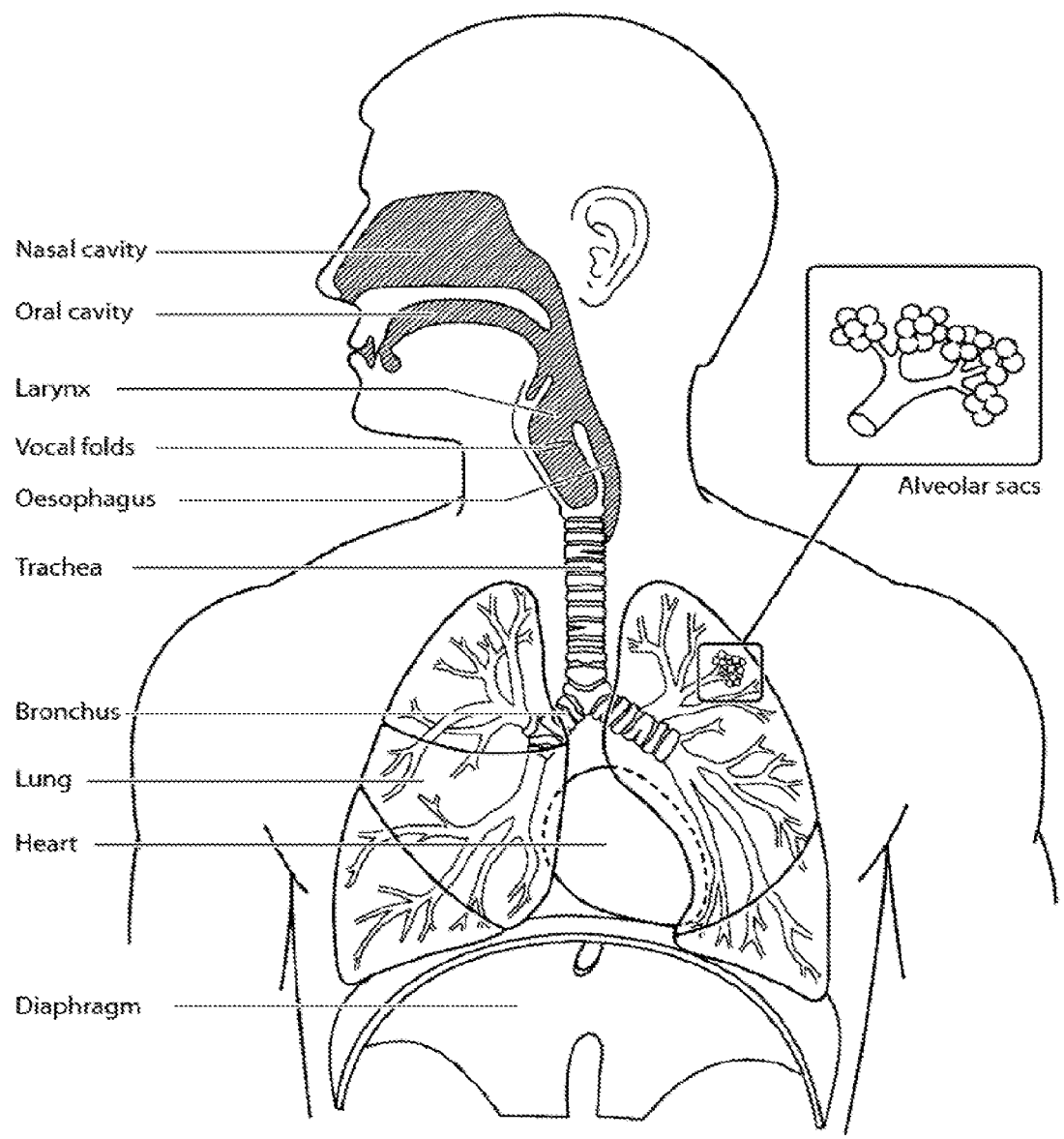
FIG. 2 shows an overview of a human respiratory system including the nasal and oral cavities, the larynx, vocal folds, oesophagus, trachea, bronchus, lung, alveolar sacs, heart and diaphragm.

The system 3000 may further comprise a respiratory effort sensor 3050 on a chest or abdominal band 3055, similar to the respiratory inductance plethysmogram (respiratory effort sensor) 2040 in the PSG system of FIG. 2. The respiratory effort sensor 3050 is connected to the processor 3030, either directly (for a digital sensor 3050) or via an A/D converter (for an analog sensor 3050) with a predetermined sampling frequency, e.g., 10 Hz. The processor 3030 may be further configured to process and/or analyze the respiratory effort signal generated by the respiratory effort sensor 3050 as described below.

The system 3000 may further comprise an actigraph 3060. An actigraph is an accelerometer configured to generate signals representing the acceleration of the actigraph in each of three orthogonal axes, labelled X, Y, and Z, and defined in relation to the axes of the actigraph. These three signals are collectively referred to as the actigraphy signal. Actigraphy has been widely used by researchers as an input to sleep/wake determination in a variety of scenarios, most frequently for the evaluation of insomnia, sleep state misperception, and circadian rhythm disorders. Because actigraphy is not acquired using electrophysiology, but rather by quantification of movement, disagreement between sleep/wake states derived from PSG and actigraphy is possible when patients frequently toss and turn during sleep or experience motionless awakenings. Several algorithms for analysis of actigraphy have been developed and applied in different situations; concordance of sleep/wake results obtained from these algorithms with those obtained using the gold-standard PSG is generally good.

The actigraph 3060 is configured to be mounted on a convenient location on the patient's body, for example on the patient's trunk. The actigraph 3060 is connected to the processor 3030, either directly (for a digital actigraph 3060) or via an A/D converter (for an analog actigraph 3060) with a predetermined sampling frequency, e.g. 10 Hz. Either the actigraph 3060 (if digital) or the A/D converter is said to generate actigraphy data or an actigraphy signal comprising samples at a certain sampling frequency. The processor 3030 may be further configured to process and/or analyze the actigraphy signal generated by the actigraph 3060 as described below.

The system 3000 may further comprise a power source 3090, such as a battery, configured to generate power for the other components of the system 3000. The system may also use other power sources such as that available via an A/C outlet.

As mentioned above, the signal processing/analysis may be carried out by the processor 3030. The processor may comprise a processor specifically programmed to carry out the monitoring/processing/analysis/diagnosis or any of the other methods discussed herein, including those relating to, for example, SDB. In such implementations of the system 3000, the processing may be embodied as computer programs stored in the memory 3080. Such computer programs may comprise instructions and/or data to carry out the algorithms or methods disclosed herein. The programs may be stored in a memory location, e.g., ROM, and then get loaded in RAM during run time as needed. The processor may also comprise a digital signal processor or an application specific integrated circuit appropriately programmed (e.g., with code downloaded from a storage location or burnt into the hardware) to implement the algorithms and methods discussed herein.

The processor that carries out the signal processing/analysis may alternatively form part of a remote computing device (not shown). In one such implementation, processor 3030 may be a "local processor" configured to relay the signals generated by the various sensors, e.g. the breathing sensor 3010, to a processor associated with a remote computing device ("the remote processor"), either wirelessly or by wired connection, via a communication interface 3070. In such an implementation, the system 3000 may communicate via BlueTooth or WiFi with the remote computing device, for example a laptop, mobile phone, tablet or, more generally, any computing device with sufficient processing capability. In another such implementation, the processor 3030 may store the various signals in the memory 3080, which may be removable from the system 3000 (such as for example a memory card or external hard drive, etc.). In such an implementation, the removed memory 3080 may be inserted in an interface of the remote computing device, which is configured to retrieve the stored signals from the memory 3080 for processing/analysis by its processor (the remote processor). The memory that stores the actigraph data or signals used by a processor in performing the algorithms or methods described herein may therefore be different than the memory that stores the program used to store instructions, or in some implementations it could be the same memory.

The signal processing/analysis may also be shared between the local processor 3030 and the processor of the remote computing device, such that some portion of the signal processing/analysis is carried out by the local processor 3030, which then sends intermediate analysis results to the remote computing device so that the remainder of the signal processing/analysis may be carried out by the processor of the remote computing device.

The breathing sensor 3010, processor 3030, A/D converter 3040, communication interface 3070, and memory 3080 of the system 3000 are housed in a housing 3095. The housing 3095 is preferably of a hand-held or pocket size so that it can easily be carried and used by a patient.

8.1.3 Signal Processing/Analysis

The following sections describe various aspects of the signal processing/analysis carried out on the various signals as part of the screening/diagnosis/monitoring function of the system 3000.

8.1.3.1 Total Sleep Time Estimation

According to some aspects of the disclosure, a total sleep time estimation method may use an activity-based classifier capable of discriminating sleep from wakefulness periods during a monitoring session while the patient is in bed. The total sleep time estimation method may be a supervised learning type method that uses a training dataset to "learn" parameters. In one implementation, the total sleep time estimation method takes the triaxial acceleration signals making up the actigraphy signal generated by the actigraph 3060 during the monitoring session, filters them appropriately, and partitions the monitoring session into epochs. A count of physical activity is estimated for each epoch from the filtered actigraphy signal. Each epoch is classified into a binary state, either "sleep" or "wake", based on the activity counts. The classification uses activity thresholds that may, for example, have been optimised via cross-validation on previously "scored" training data.

FIG. 5 contains a flow chart illustrating an example or a total sleep time estimation method 500, according to one form of the present technology. Method 500 may be implemented, for example, by local processor 3030 shown in FIG. 3 or by a remote processor, or by a combination of local processor 3030 and a remote processor, as described above.

The method 5000 starts at step 5010, which pre-processes the actigraphy signal. Pre-processing the actigraphy signal may include, for example, removing any drift in the baseline of the accelerometer. In accordance with some implementations, pre-processing may include de-trending the actigraphy signal. Step 5020 then filters the pre-processed actigraphy signal. Each of steps 5010 to 5030 are carried out independently on the three "channels" of the actigraphy signal, that is, the acceleration values in each of the three axes (X, Y, and Z).

After pre-processing, the resulting pre-processed signal may be filtered, as shown at 5020. Filtering may include, for example, reducing or removing components of the actigraphy signal unrelated to gross bodily motion. In one implementation, step 5020 comprises band-pass filtering the de-trended actigraphy signal within the range 0.5 Hz to 4.5 Hz, which corresponds to a range of normal gross bodily movement. Step 5020 may also comprise magnitude normalisation, in which the filtered actigraphy signal is divided by its 95th percentile value.

Step 5030 follows, which partitions each channel into epochs of predetermined durations. In one implementation, each epoch is of duration 30 seconds, and each epoch overlaps the previous and succeeding epoch by ten seconds in order to minimise marginal cases. It is noted, however, that other epoch durations and overlap ranges may be selected.

The next step 5040 determines an activity count $A_n$ for each epoch n. In one implementation, step 5040 rectifies (e.g., takes the absolute value of) the three filtered actigraphy channels, sums the three rectified channels to obtain a single actigraphy signal, and computes the activity count $A_n$ for each epoch as a quadratic mean (RMS value or root mean square) of the summed signal over the epoch.

The method 5000 then proceeds to step 5050, which determines a sleep/wake state of each epoch n based on its activity count $A_n$ and that of its preceding epoch ($A_{n-1}$). In one implementation, if the ratio of $A_n$ to $A_{n-1}$ exceeds a first activity threshold $T_1$, the sleep/wake state of epoch n is determined to be "wake"; otherwise, it is "sleep". In such an implementation, the patient is determined to be asleep if the activity count has not increased substantially since the previous epoch, regardless of its absolute level. In another implementation, if the activity count $A_n$ is greater than a second activity threshold $T_2$, the sleep/wake state of epoch n is determined to be "wake", otherwise, it is "sleep". In yet another implementation, if either of these criteria are met, the sleep/wake state of epoch n is determined to be "wake", otherwise, it is "sleep".

The activity thresholds $T_1$ and $T_2$ may be determined from previous actigraphy data that has been "scored" (i.e. sleep/wake state determined) by some other means, e.g., manually using simultaneous PSG data. In one implementation, the optimisation of the activity thresholds may be carried out by six-fold cross-validation, maximising cross-correlation coefficients between the output of the method 5000 and the scored actigraphy data. In one such implementation on typical scored actigraphy data, the optimal value of the first activity threshold $T_1$ was found to be 1.7, and the optimal value of the second activity threshold $T_2$ was found to be the $94^{th}$ percentile of activity counts over the scored data set. However, values of the first activity threshold in the range [1.3, 2.0], and of the second activity threshold in the range between the $65^{th}$ and the $98^{th}$ percentile, may be used with reasonable efficacy.

The final step 5060 estimates the total sleep time (TST) from the determined sleep/wake state of each epoch. Since the epochs are overlapping, step 5060 does not simply count the number of sleep-determined epochs and multiply by the duration of each epoch. Rather, step 5060 counts the number of time instants corresponding to actigraphy signal samples that have been determined to be part of an epoch whose sleep/wake state was determined to be "sleep", and divides by the sampling frequency of the actigraph 3060 or its A/D converter (whichever of these supplies the actigraphy signal samples to the signal processing/analysis). The result is a TST value in seconds.

An alternative implementation of the total sleep time estimation method uses either the respiratory flow rate signal from the breathing sensor 3010 or the respiratory effort signal from the respiratory effort sensor 3050 in addition to the actigraphy signal from the actigraph 3060.

FIG. 6 contains a flow chart illustrating a method 6000 that may be used to implement the total sleep time estimation method according to the alternative implementation. Steps 6010 to 6040 of the method 6000 are the same as the corresponding steps 5010 to 5040 in the method 5000.

Step 6050, like step 5050, determines a sleep/wake state of each epoch n. Step 6050, like step 5050, uses the activity count $A_n$ of the epoch and that of its preceding epoch ($A_{n-1}$). Unlike step 5050, step 6050 further takes into account either the respiratory flow rate signal from the breathing sensor 3010 or the respiratory effort signal from the respiratory effort sensor 3050. This additional signal provides further insights into the state of the patient, particularly during epochs when the patient may have been awake but relatively motionless.

FIG. 7 contains a flow chart illustrating a method 7000 that may be used to implement the total sleep time estimation step 6050 of the method 6000 for a current epoch n. The method 7000 is described in terms of the respiratory flow rate signal from the breathing sensor 3010, but it should be understood that the method 7000 may also be carried out with the respiratory effort signal from the respiratory effort sensor 3050 substituted for the respiratory flow rate signal.

The method 7000 starts at step 7010, which checks, like step 5050, whether the ratio ($A_n/A_{n-1}$) of the activity count $A_n$ of the current epoch to the activity count $A_{n-1}$ of the preceding epoch exceeds a first activity threshold $T_1$, or whether the activity count $A_n$ of the current epoch is greater than a second activity threshold $T_2$. If so ("Y"), step 7020 determines the sleep/wake state of the current epoch n to be "wake". The same activity thresholds $T_1$ and $T_2$ may be used in step 7010 as in step 5050.

However, if neither of these conditions holds ("N"), although the patient is relatively immobile, the method 7000 makes further checks before determining the sleep/wake state. In particular, step 7030 determines whether the quality of the respiratory flow rate signal during the current epoch is sufficient. If not ("N"), step 7040 determines the sleep/wake state of the current epoch to be "unknown". Otherwise ("Y"), step 7050 determines whether the respiratory flow rate signal during the current epoch is stable. To test for stability, step 7050 tests whether the variability (e.g. standard deviation) over the epoch of one or more of the following respiratory-flow-rate-related variables is below a threshold:

Tidal volume;
Inspiratory time;
Respiratory rate;
Inspiratory peak flow;
Expiratory peak flow location;
Time since last breath.

If the respiratory flow rate signal during the current epoch is stable ("Y"), step 7060 determines the sleep/wake state of the current epoch to be "sleep". Otherwise ("N"), step 7070 determines whether the respiratory flow rate signal contains an indication that an SDB event took place during the current epoch. "SDB events" in this context refers to breathing events related to sleep-disordered breathing and may include snore, flow limitation, respiratory-effort-related arousal, obstructive hypopnea, and obstructive apnea. Methods of detecting these various kinds of SDB events are described below. If so ("Y"), step 7060 determines the sleep/wake state of the current epoch to be "sleep". Otherwise, step 7080 determines the sleep/wake state of the current epoch to be "wake".

The final step 6060 of the method 6000 estimates the total sleep time (TST) from the sleep/wake determination of each epoch in the same way as step 5060 of the method 5000.

8.1.3.2 Apnea/Hypopnea Detection

The apnea/hypopnea detection algorithm receives as an input a signal representing the respiratory flow rate from the breathing sensor 3010 and provides as an output a flag that indicates that an apnea or a hypopnea has been detected.

In one form, an apnea will be said to have been detected when a function of respiratory flow rate falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

8.1.3.3 Detection of Snore

In one form, the snore detection algorithm receives as an input a respiratory flow rate signal from the breathing sensor 3010 and provides as an output a metric of the extent to which snoring is present.

The snore detection algorithm may comprise the step of determining the intensity of the flow rate signal in the range of 30-300 Hz. Further, the snore determination algorithm may comprise a step of filtering the respiratory flow rate signal to reduce background noise, e.g., the sound of airflow in the system from the blower.

If the intensity of the filtered respiratory flow rate signal exceeds a threshold, snore may be said to be present.

8.1.3.4 Determination of Airway Patency

Patency is the degree of the airway being open, or the extent to which the airway is open. A patent airway is open. Airway patency may be quantified, for example with a value of one (1) being patent, and a value of zero (0), being closed (obstructed). An apnea or hypopnea that coincides with a patent airway is said to be an open apnea or hypopnea; an apnea or hypopnea that coincides with a closed airway is said to be an obstructive apnea or hypopnea.

In one form, the airway patency determination algorithm receives as an input a respiratory flow rate signal, and determines the power of the signal in the frequency range of about 0.75 Hz and about 3 Hz. The presence of a peak in this frequency range is taken to indicate an open airway. The absence of a peak is taken to be an indication of a closed airway.

In one form, airway patency determination algorithm receives as an input a respiratory flow rate signal, and determines the presence or absence of a cardiogenic signal. The absence of a cardiogenic signal is taken to be an indication of a closed airway.

8.1.3.5 Detection of Flow Limitation

Flow limitation may be detected from the respiratory flow rate signal as described in U.S. Provisional Patent Application No. 62/043,079, filed 28 Aug. 2014, by ResMed Limited, titled "Diagnosis and treatment of Respiratory Disorders".

8.1.3.6 Detection of RERAs

RERAs may be detected from the respiratory flow rate signal as described in PCT Patent Application no. PCT/

AU2015/050056, filed 13 Feb. 2015 by ResMed Limited, titled "Diagnosis and treatment of Respiratory Disorders".

8.1.3.7 AHI Computation

The apnea/hypopnea index (AHI) may be computed as follows:

$$AHI = \frac{\text{number of apneas or hypopneas during the session}}{\text{total sleep time (TST) of the session (in hours)}}$$

The AHI is therefore represents the number of apnea/hypopnea events experienced (or detected) per hour of sleep. Conventionally, the AHI is taken as an indicator of the severity of a person's sleep-disordered breathing. Consequently, treatment decisions may be based on the value of the AHI computed by the system 3000.

8.1.3.8 Screening/Diagnosis/Monitoring

Once computed, the AHI may be used as a screening tool by singling out patients whose AHI during a screening session exceeds a certain threshold for further attention.

The AHI may also be used to diagnose a patient, that is, categorise the patient by the severity of their SDB, by placing the patient in a category depending on the value of their AHI computed during a diagnosis session.

Monitoring a patient being treated for SDB using the AHI may involve computing their AHI during each treatment session, and reporting a deterioration of the SDB (i.e., an increase in the AHI). The parameters of the treatment may even be altered depending on the AHI.

8.1.4 Example Results

In a sleep study, "scored" actigraphy data from a wrist-mounted actigraph (Actiwatch®, available from Philips Respironics), was recorded in parallel with actigraphy data from a system 3000 with the actigraph 3060 placed on the trunk of each patient. The scored data consisted of 36 monitoring sessions of 29 different patients, comprising a total of over nine million epochs. Table 1 below contains the confusion matrix between sleep/wake states determined by the algorithm 5000 described above (i.e. without the respiratory flow rate or effort data) applied to the actigraphy data recorded by the system 3000, and the scored sleep/wake states of the parallel recorded actigraphy data.

TABLE 1

Confusion matrix between algorithm results and scoring

| Determined sleep/wake state | Scoring | | |
|---|---|---|---|
| | Sleep | Wake | Total |
| Sleep | 'True sleep' (TS) 8,123,600 | 'False wake' (FW) 407,650 | TS + FW 8,531,250 |
| Wake | 'False sleep' (FS) 493,500 | 'True wake' (TW) 410,850 | FS + TW 904,350 |
| Total | TS + FS 8,617,100 | FW + TW 818,500 | 9,435,600 |

The resulting sensitivity and specificity values are given in Table 2.

TABLE 2

Sensitivity and specificity of algorithm

| Sensitivity (%) | Specificity (%) | Accuracy (%) |
|---|---|---|
| 94.27 | 50.20 | 90.45 |

FIG. 8 contains a graph 8000 of TST estimated using the algorithm 5000 on the actigraphy data plotted against the scored TST values for the 36 monitoring sessions. The graph 8000 shows a near-linear correlation between the estimated TST and the scored TST. The overall correlation coefficient was 0.9914. Table 3 gives statistical comparison data between the estimated and scored TST values over the 36 sessions.

TABLE 3

Comparison between scored and estimated TST

| | TST (minutes) (Mean ± std. dev) |
|---|---|
| Scored | 395 ± 75.08 |
| Estimated | 398.9 ± 76.39 |
| Difference (Mean ± std. dev) | 3.9 ± 1.31 |

Table 3 shows that TST was slightly overestimated by the algorithm 5000 compared to the scored data. This may be because the two actigraphs were placed at different parts of the body (wrist vs trunk). One overestimation scenario could be, for example, when the patient was reading a book, the patient's trunk could be near-motionless but the patient's wrist could undergo motion such as turning over pages etc.

8.2 BREATHING WAVEFORMS

FIG. 9A shows polysomnography of a patient during non-REM sleep breathing normally over a period of about ninety seconds, with about 34 breaths. The top channel shows oximetry ($SpO_2$), the scale has a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

FIG. 9B shows polysomnography of a patient with SDB over a period of about six minutes. There are eleven signal channels from top to bottom with a 6 minute horizontal span. The top two channels are both EEG (electoencephalogram) from different scalp locations. Periodic spikes in the second EEG represent cortical arousal and related activity. The third channel down is submental EMG (electromyogram). Increasing activity around the time of arousals represents genioglossus nerve recruitment. The fourth & fifth channels are EOG (electro-oculogram). The sixth channel is an electocardiogram. The seventh channel shows pulse oximetry ($SpO_2$) with repetitive desaturations to below 70% from about 90%. The eighth channel is respiratory airflow using nasal cannula connected to a differential pressure transducer. Repetitive apneas of 25 to 35 seconds alternate with 10 to 15 second bursts of recovery breathing coinciding with EEG arousal and increased EMG activity. The ninth channel shows movement of chest and the tenth shows movement of abdomen. The abdomen shows a crescendo of movement over the length of the apnea leading to the arousal. Both become untidy during the arousal due to gross body movement during the recovery hyperpnea. The apneas are therefore obstructive, and the condition is severe. The lowest channel is posture, and in this example it does not show change.

8.3 GLOSSARY

For the purposes of the present technology disclosure, in certain forms of the present technology, one or more of the following definitions may apply. In other forms of the present technology, alternative definitions may apply.

8.3.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

Respiratory Pressure Therapy (RPT): The application of a supply of air to an entrance to the airways at a treatment pressure that is typically positive with respect to atmosphere.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

8.3.2 Aspects of the Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system. Respiratory flow rate, Qr, is the flow rate of air that is received into the patient's respiratory system.

Hypopnea: Preferably, a hypopnea will be taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal flow rate.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, airflow rate, patient airflow rate, respiratory airflow rate (Qr): These synonymous terms may be understood to refer to the RPT device's estimate of respiratory airflow rate, as opposed to "true respiratory flow" or "true respiratory airflow", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

8.4 OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications or other materials (e.g., unpublished patent applications) mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

8.5 REFERENCE SIGNS LIST patient 1000
headbox 2000
ground electrode 2010
EOG electrode 2015
EEG electrode 2020
ECG electrode 2025
submental EMG electrode 2030
snore sensor 2035
respiratory inductance plethysmogram 2040
respiratory inductance plethysmogram 2045
oro-nasal cannula 2050
photoplethysmograph 2055
body position sensor 2060
screening/diagnosis/monitoring system 3000
breathing sensor 3010
nasal cannula 3020
prongs 3025
flexible catheter 3028
processor 3030
A/D converter 3040
respiratory effort sensor 3050
abdominal band 3055
actigraph 3060
communication interface 3070
memory 3080
energy source 3090
housing 3095
method 5000
step 5010
step 5020
step 5030
step 5040
step 5050 step 5060
method 6000
step 6010
step 6050
step 6050
step 6060
method 7000
step 7010
step 7020
step 7030
step 7040
step 7050
step 7060
step 7070
step 7080
graph 8000

The invention claimed is:

1. A method for a medical screening device for estimating a total sleep time of a patient during a monitoring session the medical screening device comprising a plurality of sensors including an actigraph, the medical screening device being configured to be mounted, when in use, on the patient's body during sleep, the method performed by one or more processors of the screening device and/or in communication with the screening device and comprising:
receiving, by the one or more processors, an actigraphy signal generated by the actigraph during the monitoring session;
determining, by the one or more processors, an activity count for each epoch of a plurality of overlapping epochs of the monitoring session, from the actigraphy signal, wherein the plurality of overlapping epochs includes at least one overlapping epoch that overlaps a previous epoch and a succeeding epoch;
determining, by the one or more processors, a sleep/wake state of the patient during each epoch of the plurality of overlapping epochs of the monitoring session by processing the actigraphy signal; and
computing an estimate, by the one or more processors, of the total sleep time from the determined sleep/wake state of the patient during each epoch of the monitoring session, wherein the determining, by the one or more processors, the sleep/wake state of the patient during each epoch comprises:
determining a result of comparing, by the one or more processors, a ratio of the activity count of two overlapping epochs, to a first activity threshold, the ratio of the activity count of two overlapping epochs being a ratio of the activity count for an overlapping epoch to the activity count for a previous epoch that immediately precedes and overlaps with the overlapping epoch, and
determining, by the one or more processors, the sleep/wake state of the patient during the overlapping epoch based at least in part on the result of the comparing.

2. The method of claim 1, further comprising filtering, by the one or more processors, the actigraphy signal to limit the signal to a predetermined frequency range corresponding to a range of normal gross body movement.

3. The method of claim 1, further comprising partitioning, by the one or more processors, the actigraphy signal into the plurality of overlapping epochs.

4. The method of claim 1, wherein the determining the sleep/wake state of the patient during the epoch further comprises determining the sleep/wake state of the patient during the overlapping epoch to be "wake" based at least in part on whether the result of the comparing indicates that the ratio of the activity count for the overlapping epoch to the activity count for the previous epoch is greater than the first activity threshold.

5. The method of claim 1, wherein the determining the sleep/wake state of the patient during the epoch further comprises determining the sleep/wake state to be "wake" based at least in part on whether the activity count of the epoch is greater than a second activity threshold.

6. The method of claim 1, wherein the determining the sleep/wake state further depends on a respiratory flow rate signal of the patient.

7. The method of claim 6, wherein the determining the sleep/wake state further comprises determining the sleep/wake state to be "sleep" if the respiratory flow rate signal is stable during the epoch.

8. The method of claim 6, wherein the determining the sleep/wake state further comprises determining the sleep/wake state to be "sleep" if the respiratory flow rate signal contains an indication that a sleep-disordered breathing (SDB) event took place during the epoch.

9. The method of claim 1, wherein the determining the sleep/wake state further depends on a respiratory effort signal of the patient.

10. The method of claim 9, wherein the determining the sleep/wake state further comprises determining the sleep/wake state to be "sleep" if the respiratory effort signal is stable during the epoch.

11. The method of claim 9, wherein the determining the sleep/wake state further comprises determining the sleep/wake state to be "sleep" if the respiratory effort signal contains an indication that a sleep-disordered breathing (SDB) event took place during the epoch.

12. The method of claim 8, wherein the SDB event comprises one of snore, flow limitation, respiratory-effort-related arousal, obstructive hypopnea, and obstructive apnea.

13. The method according of claim 1, further comprising computing an index of severity of sleep-disordered breathing of the patient from the estimated total sleep time.

14. The method according to claim 13, wherein the computing the index comprises
detecting apneas and hypopneas during the session, and
dividing a number of detected apneas and hypopneas during the session by the estimated total sleep time.

15. The method according to claim 1, wherein the determining an activity count for an epoch comprises:
rectifying, in the one or more processors, each channel of the actigraphy signal, summing, in the one or more processors, the rectified channels to obtain a single actigraphy signal, and
computing, in the one or more processors, a root mean squared value of the single actigraphy signal over the epoch.

16. A system for estimating a total sleep time of a patient during a monitoring session, the system comprising a medical screening device including a plurality of sensors, the medical screening device being configured to be mounted on the patient's body during sleep, the system comprising:
an actigraph of the plurality of sensors, configured to generate an actigraphy signal representing acceleration of the actigraph in each of three orthogonal axes; and
one or more processors of the screening device and/or in communication with the screening device, the one or more processors configured to:
receive, from the actigraph, the actigraphy signal;
determine an activity count for each epoch of a plurality of overlapping epochs, from the actigraphy signal, wherein the plurality of overlapping epochs includes at least one overlapping epoch that overlaps a previous epoch and a succeeding epoch;

determine a sleep/wake state of the patient during each epoch of the plurality of overlapping epochs by processing the actigraphy signal; and compute an estimate of the total sleep time from the sleep/wake state of the patient during each epoch, wherein the one or more processors are configured to determining the sleep/wake state of the patient during each epoch by:

determining a result of comparing a ratio of the activity count of two overlapping epochs, to a first activity threshold, the ratio of the activity count of two overlapping epochs being a ratio of the activity count for an overlapping epoch to the activity count for a previous epoch that immediately precedes and overlaps with the overlapping epoch, and determining the sleep/wake state of the patient during the overlapping epoch based at least in part on the result of the comparing.

17. The system of claim 16, wherein the one or more processors are configured to filter the actigraphy signal to limit the signal to a predetermined frequency range corresponding to a range of normal gross body movement.

18. The system of claim 16, wherein the one or more processors are configured to partition the actigraphy signal into the plurality of overlapping epochs.

19. The system of claim 16, wherein the one or more processors are configured to determine the sleep/wake state of the patient during the overlapping epoch to be "wake" based at least in part on whether the result of the comparing indicates that the ratio of the activity count for the overlapping epoch to the activity count for the previous epoch is greater than the first activity threshold.

20. The system according to claim 16, further comprising a breathing sensor configured to generate a signal indicative of the patient's breathing, wherein determination of the sleep/wake state further depends on the generated signal.

21. The system according to claim 16, further comprising a respiratory effort sensor configured to generate a signal indicative of the patient's respiratory effort, wherein determination of the sleep/wake state further depends on the generated respiratory effort signal.

22. The system according to claim 16, wherein a processor of the one or more processors forms part of a remote computing device.

23. The system according to claim 22, further comprising:
a communication interface, and
wherein a local processor of the one or more processors is configured to relay the actigraphy signal to the processor of the remote computing device via the communication interface.

24. The system according to claim 22, further comprising a removable memory configured to store the actigraphy signal.

* * * * *